United States Patent
Jung et al.

(10) Patent No.: US 6,911,552 B2
(45) Date of Patent: Jun. 28, 2005

(54) PREPARATION METHOD OF ALKYLDICHLOROSILANES

(75) Inventors: Il Nam Jung, Seoul (KR); Bok Ryul Yoo, Gyeonggi-Do (KR); Joon Soo Han, Seoul (KR); Weon Cheol Lim, Seoul (KR); Mu Yeol Kim, Gwangju (KR)

(73) Assignee: Korea Institute of Science and Technology, Seoul (KR)

( * ) Notice: Subject to any disclaimer, the term of this patent is extended or adjusted under 35 U.S.C. 154(b) by 126 days.

(21) Appl. No.: 10/335,084

(22) Filed: Dec. 31, 2002

(65) Prior Publication Data

US 2003/0166958 A1 Sep. 4, 2003

(30) Foreign Application Priority Data

Jan. 30, 2002  (KR) .......................................... 2002-5452

(51) Int. Cl.$^7$ .................................................. A07F 7/16
(52) U.S. Cl. .............. 556/472; 252/186.24; 252/182.33
(58) Field of Search ................................ 556/472, 473, 556/474, 477, 478; 252/182.33, 186.24

(56) References Cited

U.S. PATENT DOCUMENTS

| 3,454,616 A | * | 7/1969 | Takamizawa et al. ....... 556/473 |
| 4,973,725 A | * | 11/1990 | Lewis et al. ................. 556/472 |
| 6,215,012 B1 | * | 4/2001 | Ueno et al. ................. 556/472 |

* cited by examiner

*Primary Examiner*—Johann Richter
*Assistant Examiner*—Chukwuma Nwaonicha
(74) *Attorney, Agent, or Firm*—Darby & Darby

(57) ABSTRACT

A method for preparing alkyldichlorosilanes having a Si—H bond by directly reacting metallic silicon with a mixture of alkyl chloride and (i) hydrogen chloride, or (ii) an alkyl chloride which can generate hydrogen chloride at a reaction temperature in the presence of copper catalyst.

6 Claims, No Drawings

PREPARATION METHOD OF ALKYLDICHLOROSILANES

BACKGROUND OF THE INVENTION

1. Field of the Invention

The present invention relates to a preparation method of alkyldichlorosilanes by directly reacting metallic silicon with a mixture of alkyl chloride and (i) hydrogen chlorides, or (ii) an alkyl chloride which can generate hydrogen chloride at the reaction temperature in the presence of copper catalyst.

2. Description of the Background Art

Since a preparation method of methylchlorosilanes by directly reacting metallic silicon with methyl chloride in the presence of copper catalyst was introduced in the U.S. Pat. No. 2,380,995, the synthesis of organosilicon compound in the current silicon industry is mostly based on the above skill. In the above reaction, a number of high boiling materials besides methylchlorosilanes are also obtained in small quantity. Also because the reaction rate and the purity of products depend on a large number of factors, e.g., the purity of the starting materials, the type of the catalyst and amount of the catalyst used, co-catalyst, the reaction temperature and pressure, the type of reactor used, the degree of silicon conversion etc., the reaction conditions for the methyl chloride reaction have been well established to obtain a title compound effectively. But still, the direct reaction of other alkyl chlorides than methyl chloride with metallic silicon has never been practiced on a large scale due to the decomposition of alkyl chlorides.

In 1955, Petrov and his co-workers reported the direct reactions of propyl chloride or butyl chloride with metallic silicon (A. D. Petrov, N, P. Smetankina, and G. I. Nikisshin. J.Gen.Chem. USSR, 1955, 25, 2305) and obtained propyldichlorosilane or butyldichlorosilane having a Si—H bond in low yields, but not dipropyldichlorosilane or dibutyldichlorosilane. The production of propyldichlorosilane and butyldichlorosilane indicates that the alkyl chlorides decomposed under the reaction conditions to give hydrogen chloride, and the alkyl chloride and hydrogen chloride simultaneously reacted with the same silicon atom.

Also, Yoshio Ono and his co-workers reported that vinyldichlorosilane or isopropyldichlorosilane could be synthesized by reacting a mixture of ethylene or propylene and hydrogen chloride with elemental silicon, but the yield was low. They also reported that isopropyldichlorosilane and normal propyldichlorosilane could be obtained by reacting a mixture of propylene and hydrogen chloride with activated silicon contact mixture containing 3% by weight of copper at 500°C. for 10 minutes (M. Okamoto, S. Onodera, Y. Yamamoto, E. Suzuki, Y. Ono, J. Chem. Soc., Dalton Trans., 2001. 71–78).

The present inventors found that organodichlorosilanes having Si—H bond could be obtained when a mixture of organic chlorides other than methyl chloride and hydrogen chloride is reacted with elemental silicon due to the reaction of both organic chloride and hydrogen chloride with the same silicon atom. For instance, when a mixture of methylene chloride and hydrogen chloride is reacted with silicon, one mole of methylene chloride and two moles of hydrogen chloride react with a same silicon atom to give bis (dichlorosilyl)methane (Jung et al., U.S. Pat. No. 5,235,083 (Aug. 10, 1993)). When a mixture of chloroform and hydrogen chloride is reacted with silicon, one mole of chloroform and three moles of hydrogen chloride react with a same silicon atom to give tris(dichlorosilyl)methane (Jung et al., U.S. Pat. No. 5,332,849(Jul. 26, 1994)). Similarly, when a mixture of allyl chloride and hydrogen chloride is reacted with silicon, one mole of allyl chloride and one mole of hydrogen chloride react with a same silicon atom to give allyldichlorosilane (Jung et al., U.S. Pat. No. 5,338,876 (Aug. 16, 1994)). In the above reactions, the decomposition of starting organic chloride was suppressed and products having Si—H bonds were obtained by adding hydrogen chloride as a raw material. Alkyl chlorides which can generate hydrogen chloride by decomposition at the reaction temperature could be also used instead of hydrogen chloride.

In a direct reaction of metallic silicon and organic chloride, it is well known that the reactions do not proceed without catalysts, and the preferred catalyst is copper. If necessary, metals as Zn, Al, Cd and the like can be used as a co-catalyst. If the amount of the copper catalyst is increased, the reaction becomes faster but the content of chlorine in products increases. Therefore, copper is generally used in about 10% or less by weight for the weight of silicon in the reaction of silicon and methyl chloride.

On the other hand, when methyl chloride was directly reacted with silicon, if metal complex of organic phosphin was added, methylchlorosilanes could be synthesized in a higher yield with an excellent selectivity (S. Ueno, T. Shinohara, M. Aramata, Y. Tanifuji, T. Inukai, K. Fujioka, U.S. Pat. No. 6,215,012(Oct. 4, 2001)). Also, since the reaction of silicon with alkyl chloride was an exothermic reaction, if the heat of reaction could not be efficiently controlled, or if a proper reaction temperature was not maintained, the reaction materials were coagulated and a partly overheated state was formed (A. L. Klebamskii and V. S. Fikhtengolts, J. Gen. Chem. U.S.S.R, 1957, 27, 2693). Furthermore, it was reported that a excessively high reaction temperature gave more by-products as well as the preferred alkyldichlorosilanes, thereby alkyl chlorides of starting materials and products were decomposed causing the deposition of carbon on the surface of silicon, and accordingly activity of silicon was rapidly decreased (J. C. Vlugter, and R. J. H. Voorhoeve, Conf. Accad. Lincei, Alta Tech. Chim. 1962, 81).

The common disadvantage of these methods arises from the facts that since the composition of the products are largely affected by the reaction condition, this condition must be carefully determined to obtain the desired products effectively; economic efficiency is degraded by the low yield; and raw materials are rapidly decomposed to give much amount of by-products. The present inventors of the invention have studied a method for preparing alkyldichlorosilanes in a higher yield with restraining generation of the by-products. As a result, the present inventors found an improved method for preparing alkyldichlorosilanes by directly reacting metallic silicon with a mixture of alkyl chloride and hydrogen chloride or alkyl chlorides which can generate hydrogen chloride at the reaction temperature.

SUMMARY OF THE INVENTION

Therefore, an object of the present invention is to provide a method for preparing alkyldichlorosilanes in a higher yield by directly reacting a mixture of alkyl chlorides and hydrogen chloride with metallic silicon.

Another object of the present invention is to provide a method for simultaneously preparing alkyldichlorosilanes and alkyltrichlorosilanes.

The foregoing and other objects, features, aspects and advantages of the present invention will become more apparent from the following detailed description and examples of the present invention.

DETAILED DESCRIPTION OF THE PREFERRED EMBODIMENTS

The present invention is to provide a method for preparing alkyldichlorosilanes (Formula 3) having a Si—H bond in a higher yield by directly reacting a mixture of alkyl chloride (Formula 1) having three or more carbon atoms and hydrogen chloride or alkyl chlorides (Formula 2) which can generate hydrogen chloride at a reaction temperature with metallic silicon in the presence of copper catalyst (Scheme 1).

Wherein, R is a linear, branched or cyclic $C_{3-10}$ of alkyl group. $R^1$ is hydrogen or $C_{4-6}$ alkyl group. Specific examples of the alkyl chloride which can generate hydrogen chloride at a reaction temperature include n-butyl chloride, t-butyl chloride and cyclohexyl chloride.

More specifically, the present invention is to provide a method for preparing alkyldichlorosilanes of Formula 3 by directly reacting a mixture of alkyl chloride and hydrogen chloride or alkyl chloride of Formula 2 which generates hydrogen chloride due to decomposition during the reaction, with metallic silicon using a fluidized bed reactor or a stirred reactor equipped with a spiral band agitator at the temperature between 200 and 350° C. Also, alkyltrichlorosilanes of Formula 4 to be a raw material of silicate can be additionally obtained by the reaction.

Linear, branched or cyclic $C_{3-10}$ alkyl chloride of Formula 1 and hydrogen chloride or alkyl chloride of Formula 2 (which is decomposed during the reaction and generates hydrogen chloride) can be mixed under the gas state with metallic silicon, or a compound of Formula 2 can be incorporated and mixed to the compound of Formula 1 in the liquid state. The compounds of Formula 1 and Formula 2 may be mixed with any ratio by weight or by volume. Generally, the amount of Formula 3 compound in the products increases with increase of Formula 2 compound addition. The compound of Formula 2 may be mixed with alkyl chloride of Formula 1 in the mole ratio of 0.1~8:1, and more preferably 1~7:1 in order to increase a yield of the Formula 3 compound.

A reactor used in the present invention is preferably a stirred reactor or fluidized bed reactor, and the reaction may be performed in batch operations or in a continuous process. Commercial silicon having a purity of 95% or more, and preferably 98% or more may be used as the elemental silicon. The size of the silicon powder which is proper for the reaction is preferably from 1 to 325 mesh, but the proper size and distribution of the silicon powder depend on the size and shape of the reactor. When a stirred reactor is used, the size of the powder may be 20~325 mesh, and more desirably 50~240 mesh.

The direct reaction according to the present invention may be carried out at the various reaction temperatures ranging from 200 to 350° C., but more preferably from 200 to 300° C. Also, the suitable reaction pressure may be between the atmospheric pressure and 5 atm, wherein the higher the pressure is, the faster the reaction speed becomes.

As the catalyst, Metal copper or copper compound which can liberate copper in the reaction condition may be used. The used amount of copper may be 1 to 20% by weight for the weight of reaction materials, and preferably 5 to 10% by weight. Provided that a co-catalyst is additionally used in an amount of 0.001 to 2% by weight for the weight of copper, the reaction becomes more faster or the selectivity for the specific product may be increased. Specific examples of co-catalyst to be proper for the reaction are given as follows, but the present invention is not limited by the examples. For instance, metal of Ni, Cd, Sn, Zn, Ca, Al, Mn, Mg, Ag, Cr and the like, or metal compounds which generate the above metals under the reaction condition may be used as the co-catalyst.

Hereinafter, the present invention will be described with reference to Examples, but the present invention is not limited by Examples.

EXAMPLE 1

Preparation of Si/Cu Contact Mixture Using Cuprous Chloride 360 g (140–200 mesh) of metallic silicon, 62.4 g of cuprous chloride (CuCl) and 20 g of micro-spherical acid clay (in order to improve flowability) were mixed well and placed in a reactor. Then the mixture was dried at 250° C. for 2 hours with stirring by dry nitrogen flush. After drying, the temperature of the reactor was raised and kept at 370° C. for 3 hours to give a Si/Cu contact mixture having a high reactivity, together with tetrachlorosilane. In case Cd, Ni, Sn, Zn and the like are used as the co-catalyst, the temperature of the reactor was lowered to the desired reaction temperature after contact mixture was generated, a predetermined amount of co-catalyst was-incorporated into the head of the reactor, and then the resultant material was stirred, mixed well and reacted.

EXAMPLE 2

Preparation of Si/Cu Contact Mixture Using Metal Copper 360 g (140–200 mesh) of metallic silicon, 40 g of copper catalyst and 20 g of micro-spherical acid clay were placed in the reactor, and dried under the condition similar to that of Example 1. After drying, the temperature of the reactor was raised to 350° C., and methyl chloride ($CH_3Cl$) was injected through a preheating tube at the bottom of the reactor. After about 40–70 minutes, dimethyldichlorosilane and methyltrichlorosilane began to be generated as the reaction products and were collected in the receiver at the bottom of the reactor. After the reaction with methyl chloride for about 3 hours, a Si/Cu contact mixture which can be properly used for the present invention is produced. In case a co-catalyst is necessary for the reaction, it may be incorporated in the same method as Example 1. Si/Cu contact mixture having different mixing ratio of catalysts was prepared, and the compositions are shown in Table 1.

TABLE 1

Composition of Si/Cu contact mixture of the present invention

| Exp. No. | Amount of Si (g) | Amount of copper type | amount (g) | Co-catalyst type | amount (g) | remarks |
|---|---|---|---|---|---|---|
| I-1 | 360 | CuCl | 62.4 | | | |
| I-2 | 360 | Cu | 40 | | | |
| I-3 | 360 | Cu | 40 | $NiCl_2(dppe)$ | 0.6 | |
| I-4 | 360 | Cu | 40 | $NiCl_2(dppb)$ | 0.6 | |

TABLE 1-continued

Composition of Si/Cu contact mixture of the present invention

| Exp. No. | Amount of Si (g) | Amount of copper | | Co-catalyst | | remarks |
|---|---|---|---|---|---|---|
| | | type | amount (g) | type | amount (g) | |
| I-5 | 360 | Cu | 40 | $NiCl_2$(dppp) | 0.6 | |
| I-6 | 360 | Cu | 40 | Sn | 2 | |
| I-7 | 360 | Cu | 40 | Cd | 2 | |
| I-8 | 360 | Cu | 40 | Zn | 2 | |

EXAMPLE 3

Effect of Reaction Temperature on the Reaction of Metallic Silicon with 1:2.5 Mixture of 2-chloropropane and Hydrogen Chloride In order to optimize the reaction temperature, the reaction was carried out as shown in the following typical experimental No. 2. 360 g of Si/Cu contact mixture (1–4) prepared in Example 2 was placed in a stirred reactor, the temperature of the reactor was raised to 220° C. and then, nitrogen gas and hydrogen chloride were flowed into the reactor and at the same time, 2-chloropropane (10 ml, 0.108 mole) was added using a syringe pump into a preheating tube of the reactor. The amount of reaction products obtained after completing the reaction was 15.1 g. The obtained reaction products were analyzed by using gas chromatography (packed column, 10% OV 101, 1.5 m×⅛" O.D., SS, TCD) and fractionally distilled to separate its constituents from one another, so that their structures could be determined. The structure of each constituent was determined by using a nuclear magnetic resonance spectrometer. The reaction products contained 8.2 g (54.7%) of 1,1-dichloro-2-methyl-1-silapropane and 0.3 g (1.7%) of 1,1,1-trichloro-2-methyl-1-silapropane. Other by-products were 5.8 g of trichlorosilane and unconfirmed materials.

1,1-dichloro-2-methyl-1-silapropane
($^1$H-NMR, $CDCl_3$, ppm): 1.15 (s, 3H, $CCH_3$), 1.17 (s, 3H, $CCH_3$), 1.34–1.39(m, 1H, $CH_3CH$), 5.39 (s, 1H, SiH)

1,1,1-trichloro-2-methyl-1-silapropane
($^1$H-NMR, $CDCl_3$, ppm): 1.18 (s, 3H, $CCH_3$), 1.20 (s, 3H, $CCH_3$), 1.48–1.58(m, 1H, $CH_3CH$)

The product compositions obtained from the reactions at various reaction temperatures using the same condition (for example, starting material, reactor, catalyst, co-catalyst etc.) are shown in Table 2.

TABLE 2

Product distributions at various reaction temperatures

| Exp. No. | Reaction temperature (° C.) | Total Amount of products (g) | Product Yield (%) | |
|---|---|---|---|---|
| | | | $III_a$ | $IV_a$ |
| 1 | 200 | 10.1 | 26.0 | 0.7 |
| 2 | 220 | 15.1 | 54.7 | 1.7 |
| 3 | 250 | 9.7 | 41.3 | 1.8 |
| 4 | 270 | 11.3 | 26.7 | 1.6 |
| 5 | 300 | 8.9 | 15.5 | 1.4 |

Amount of 2-chloropropane in use: 10 ml, reaction time: 40 minutes
$III_a$: Compound of Formula 3, wherein R is i-propyl
$IV_a$: Compound of Formula 4, wherein R is i-propyl

EXAMPLE 4

The Product Composition According to the Mixing Ratios of 2-chloropropane and Hydrogen Chloride To study the effect of hydrogen chloride addition, the reaction was carried out using the same contact mixture and method as described in Example 3, except engaging the mixing ratios of 2-chloropropane and hydrogen chloride at 220° C. This is to optimize the amount of hydrogen chloride at the reaction temperature of 220° C. where the yield of the products is highest. The results are shown in Table 3. However, the experimental No. 9 was conducted in a fluidized bed reactor under the same condition.

TABLE 3

Mixing ratios of 2-chloropropane and hydrogen chloride, and product distributions

| Exp. No. | 2-chloropropan:hydrogen chloride (mole ratio) | Total amount of products (g) | Product Yield (%) | |
|---|---|---|---|---|
| | | | $III_a$ | $IV_a$ |
| 6 | 1:0 | 8.5 | 34.1 | 2.3 |
| 7 | 1:1.5 | 10.6 | 37.6 | 2.1 |
| 8 | 1:2.5 | 15.1 | 54.7 | 1.7 |
| 9 | 1:2.5 | 9.1 | 28.3 | 2.5 |
| 10 | 1:3 | 16.6 | 35.6 | 1.9 |

Amount of 2-chloropropane in use: 10 ml, reaction time: 40 minutes
$III_a$: Compound of Formula 3, wherein R is i-propyl
$IV_a$: Compound of Formula 4, wherein R is i-propyl

EXAMPLE 5

Effect of the Catalysts on the Reaction of Metallic Silicon with a Mixture of 2-chloropropane and Hydrogen Chloride The reaction was conducted using contact mixtures of Table 1 under the same condition as described in experiment No. 2 of Example 3, and the results are shown in Table 4.

TABLE 4

Effect of catalyst and co-catalysts on product distributions

| Exp. No. | Kind of contact mixture | Total amount of products (g) | Product Yield (%) | |
|---|---|---|---|---|
| | | | $III_a$ | $IV_a$ |
| 11 | I-1 | 2.5 | 5.3 | — |
| 12 | I-2 | 9.6 | 42.1 | 7.3 |
| 13 | I-3 | 5.3 | 4.3 | 0.1 |
| 14 | I-4 | 15.1 | 54.7 | 1.7 |
| 15 | I-5 | 6.4 | 25.0 | 1.3 |
| 16 | I-6 | 0.5 | — | — |
| 17 | I-7 | 3.5 | 17.2 | 0.2 |
| 18 | I-8 | — | — | — |

Amount of 2-chloropropane in use: 10 ml, reaction time: 40 minutes
$III_a$: Compound of Formula 3, wherein R is i-propyl
$IV_a$: Compound of Formula 4, wherein R is i-propyl

EXAMPLE 6

The Product Compostion According to the Mixing Ratios of 2-chloropropane and t-butyl Chloride The present experiement was described as shown in the following typical experimental No. 20 in Table 5. The reaction was carried out under the same condition as in Example 3, except that the same amount of t-butyl chloride was used as the hydrogen chloride source. A mixture of 2-chloropropane and t-butyl chloride having the mixing ratio of 1:3 was reacted with metallic silicon to give 30.1 g of reaction products. The reaction products contained 10.2 g (66.1%) of 1,1-dichloro-2-methyl-1-silapropane and 0.66 g (7.2%) of 1,1,1-trichloro-2-methyl-1-silapropane. As one of other by-products, 13.6 g of trichlorosilane was obtained.

Table 5 shows the product compositions obtained by reacting a mixture of 2-chloropropane and t-butyl chloride with metallic silicon, only with changing the mixing ratio of 2-chloropropane and t-butyl chloride.

TABLE 5

Mixing ratios of 2-chloropropane and t-butyl chloride and product distributions

| Exp. No. | 2-chloropropane:t-butyl chloride | Total amount of products (g) | Product Yield (%) $III_a$ | $IV_a$ |
|---|---|---|---|---|
| 19 | 1:1 | 13.6 | 38.8 | 4.1 |
| 20 | 1:3 | 30.1 | 66.1 | 7.2 |
| 21 | 1:5 | 41.4 | 47.8 | 9.7 |

Amount of 2-chloropropane in use: 10 ml, reaction time: 40 minutes, reaction temperature: 220° C.
$III_a$: Compound of Formula 3, wherein R is i-propyl
$IV_a$: Compound of Formula 4, wherein R is i-propyl

EXAMPLE 7

Effect of Reaction Temperature on the Reaction of Cyclopentyl Chloride with Metallic Silicon In order to optimize the reaction temperature, the reaction was carried out as shown in the following typical experimental No. 23 in Table 6. Nitrogen gas was flowed into the reactor after raising the temperature of the reactor to 260° C. similarly with Example 3 and at the same time, cyclopentyl chloride (10 ml, 0.0942 mole) was added using a syringe pump into the preheating tube of the reactor. The total amount of reaction products obtained after completing the reaction was 8.1 g. The reaction products contained 3.4 g (21.4%) of cyclopentyldichlorosilane and 0.2 g (1.2%) of cyclopentyltrichlorosilane. Other by-products were 3.9 g (60.8%) of cyclopentene, 0.6 g of trichlorosilane, and minor unconfirmed materials.
cyclopentyldichlorosilane
($^1$H-NMR, $CDCl_3$, ppm): 1.47–1.93 (m, 9H, CyclicH), 5.43 (s, 1H, SiH)
cyclopentyltrichlorosilane
($^1$H-NMR, $CDCl_3$, ppm): 1.56–1.95 (m, 9H, CyclicH)
The product compositions obtained from the reactions at a various reaction temperatures using the same condition with the above-mentioned experiment are shown in Table 6.

TABLE 6

Product distributions at various reaction temperatures

| Exp. No. | Reaction temperature (° C.) | Total amount of products (g) | product Yield (%) $III_b$ | $IV_b$ | cyclopentene |
|---|---|---|---|---|---|
| 22 | 240 | 7.0 | 6.2 | 0.6 | 77.4 |
| 23 | 260 | 8.1 | 21.4 | 1.2 | 60.8 |
| 24 | 280 | 8.0 | 20.2 | 2.2 | 59.8 |
| 25 | 300 | 7.9 | 19.2 | 3.1 | 57.6 |

Amount of cyclopentyl chloride in use: 10 ml, reaction time: 40 minutes
$III_b$: Compound of Formula 3, wherein R is cyclopentyl
$IV_b$: Compound of Formula 4, wherein R is cyclopentyl

EXAMPLE 8

The Product Composition According to the Mixing Ratios of Cyclopentyl Chloride and Hydrogen Chloride To study the effect of hydrogen chloride addtion, the reaction was carried out using the same contact mixture and method as described in Example 3, except changing the mixing ratios of cyclopentyl chloride and hydrogen chloride at 260° C. The reaction results are shown in Table 7. However, the experimental No. 27 was conducted in a fluidized bed reactor under the same conditions.

TABLE 7

Mixing ratios of cyclopentyl chloride and hydrogen chloride, and product distributions

| Exp. No. | Cyclopentyl chloride:hydrogen chloride | Total amount of products (g) | Product Yield (%) $III_b$ | $IV_b$ | cyclopentene |
|---|---|---|---|---|---|
| 26 | 1:0 | 8.1 | 21.4 | 1.2 | 60.8 |
| 27 | 1:0 | 5.2 | 9.5 | 1.8 | 61.2 |
| 28 | 1:1 | 7.4 | 11.5 | 0.6 | 65.9 |
| 29 | 1:2 | 9.9 | 11.9 | 0.5 | 76.0 |
| 30 | 1:4 | 27.0 | 10.6 | 0.6 | 81.0 |

Amount of cyclopentyl chloride in use: 10 ml, reaction time: 40 minutes
$III_b$: Compound of Formula 3, wherein R is cyclopentyl
$IV_b$: Compound of Formula 4, wherein R is cyclopentyl

EXAMPLE 9

Effect of the Catalysts on the Reaction of Metallic Silicon with a Mixture of Cyclopentyl Chloride and Hydrogen Chloride The reaction was conducted using contact mixtures of Table 1 under the same condition as described in experiment No. 23 of Example 7, and the results are shown in Table 8.

TABLE 8

Eeffect of catalyst and co-catalysts on product distributions

| Exp. No. | Kind of contact mixture | Total amount of products (g) | product Yield (%) $III_b$ | $IV_b$ | cyclopentene |
|---|---|---|---|---|---|
| 31 | I-1 | 2.8 | 2.2 | 0.2 | 28 |
| 32 | I-2 | 4.3 | 5.6 | 0.5 | 34 |
| 33 | I-3 | 5.4 | 4.9 | 0.4 | 54.8 |
| 34 | I-4 | 8.1 | 21.4 | 1.2 | 60.8 |
| 35 | I-5 | 4.2 | 12.9 | 0.8 | 7.0 |
| 36 | I-6 | 0.7 | — | 3.3 | — |
| 37 | I-7 | 2.0 | 8.4 | 0.2 | 5.7 |
| 38 | I-8 | 1.1 | 0.3 | — | 6.1 |

Amount of cyclopentyl chloride in use: 10 ml, reaction time: 40 minutes
$III_b$: Compound of Formula 3, wherein R is cyclopentyl
$IV_b$: Compound of Formula 4, wherein R is cyclopentyl

EXAMPLE 10

The Product Composition According to the Mixing Ratios of Cyclopentyl Chloride and t-butyl Chloride The reaction was carried out under the same condition as in Example 3, except that the same amount of t-butyl chloride was used as the hydrogen chloride source. A mixture of cyclopentyl chloride and t-butyl chloride having the mixing ratio of 1:2 was reacted with metallic silicon at 280° C. to give 30.1 g of reaction products. The reaction products contained 6.2 g (39.1%) of cyclopentyldichlorosilane and 0.3 g (1.6%) of cyclopentyltrichlorosilane. There were not starting materials unreacted. As other by-products, 3.7 g (58.4%) of cyclopentene, 2.9 g of trichlorosilane and unconfirmed materials were obtained.

Table 9 shows the product compositions obtained by reacting a mixture of cyclopentyl chloride and t-butyl chloride with metallic silicon, only with changing the mixing ratios of cyclopentyl chloride and t-butyl chloride.

TABLE 9

Mixing ratios of cyclopentyl chloride and t-butyl chloride and product distributions

| Exp. No. | Cyclopentyl chloride:t-butyl chloride | Total amount of products (g) | Product Yield (%) | | |
|---|---|---|---|---|---|
| | | | $III_b$ | $IV_b$ | cyclopentene |
| 39 | 1:0.5 | 9.4 | 36.2 | 1.6 | 33.2 |
| 40 | 1:1 | 11.4 | 34.2 | 2.9 | 51.6 |
| 41 | 1:2 | 16.1 | 39.1 | 1.6 | 58.4 |
| 42 | 1:3 | 18.8 | 32.3 | 1.5 | 65.4 |

Amount of cyclopentyl chloride in use: 10 ml, reaction time: 40 minutes, reaction temperature: 280° C.
$III_b$: Compound of Formula 3, wherein R is cyclopentyl
$IV_b$: Compound of Formula 4, wherein R is cyclopentyl

EXAMPLE 11

Effect of Reaction Temperature on the Reaction of Metallic Silicon with 1:8 Mixture of 1-chlorohexane and Hydrogen Chloride In order to optimize the reaction temperature, the reaction was carried out as shown in the following typical experimental No. 45. The temperature of the reactor was raised to 280° C. in the same method as Example 3. Then, nitrogen gas and hydrogen chloride were flowed into the reactor and at the same time, 1-chlorohexane (10 ml, 0.072 mole) was added using a syringe pump into a preheating tube of the reactor. The amount of reaction products obtained after completing the reaction was 13.0 g. The reaction products contained 4.7 g (35.6%) of 1,1-dichloro-1-silaheptane and 0.9 g (5.5%) of 1,1,1-trichloro-1-silaheptane. Other by-products were 1.9 g (22.4%) of raw materials which were remained unreacted, 1.7 g (28.1%) of 1-hexene, 2.5 g of trichlorosilane, and unconfirmed material.
1,1-dichloro-1-silaheptane ($^1$H-NMR, CDCl$_3$, ppm): 0.89 (t, J=6.6 Hz, 3H, CH$_3$), 1.17–1.56 (m, 10H, (CH$_2$)$_5$CH$_3$), 5.51 (t, J=1.5 Hz, 1H, SiH)
1,1,1-trichloro-1-silaheptane ($^1$H-NMR, CDCl$_3$, ppm): 0.92 (t, J=6.9 Hz, 3H, CH$_3$), 1.31–1.61(m, 10H, (CH$_2$)$_5$CH$_3$)

The product compositions obtained from the reactions at a various reaction temperatures using the same condition with the above-mentioned experiment are shown in Table 10.

TABLE 10

Product distributions at various reaction temperatures

| Exp. No. | Reaction temperature (° C.) | Total Amount of Products (g) | Product Yield (%) | | | |
|---|---|---|---|---|---|---|
| | | | 1-chlorohexane | $III_c$ | $IV_c$ | hexene |
| 43 | 240 | 11.7 | 52.1 | 25.3 | 2.2 | 12.2 |
| 44 | 260 | 10.5 | 27.8 | 30.4 | 3.9 | 11.9 |
| 45 | 280 | 13.0 | 22.4 | 35.6 | 5.5 | 28.1 |
| 46 | 300 | 12.3 | 19.6 | 26.1 | 5.8 | 36.4 |

Amount of 1-chlorohexane in use: 10 ml, reaction time: 40 minutes
$III_c$: Compound of Formula 3, wherein R is n-hexyl
$IV_c$: Compound of Formula 4, wherein R is n-hexyl

EXAMPLE 12

The Product Composition According to the Mixing Ratios of 1-chlorohexane and Hydrogen Chloride To study the effect of hydrogen chloride addtion, the reaction was carried out using the same contact mixture and method as described in Example 3, except changing the mixing ratios of 1-chlorohexane and hydrogen chloride at 280° C. The reaction results are shown in Table 11. However, the experimental No. 52 was conducted in a fluidized bed reactor using the same conditions.

TABLE 11

Mixing ratios of 1-chlorohexane and hydrogen chloride, and product distributions

| Exp. No. | 1-chloro hexane:hydrogen chloride | Total amount of products (g) | Product Yield (%) | | | |
|---|---|---|---|---|---|---|
| | | | 1-chlorohexane | $III_c$ | $IV_c$ | hexene |
| 47 | 1:0 | 5.0 | 12.2 | 14.4 | 4.0 | 16.1 |
| 48 | 1:2 | 8.9 | 10.9 | 27.7 | 8.8 | 25.0 |
| 49 | 1:4 | 8.7 | 5.7 | 29.8 | 11.2 | 21.8 |
| 50 | 1:8 | 13.0 | 22.4 | 35.6 | 5.5 | 28.1 |
| 51 | 1:10 | 18.5 | 10.4 | 41.2 | 6.0 | 30.2 |
| 52 | 1:10 | 11.3 | 8.5 | 20.7 | 5.2 | 27.8 |

Amount of 1-chlorohexane in use: 10 ml, reaction time: 40 minutes
$III_c$: Compound of Formula 3, wherein R is n-hexyl
$IV_c$: Compound of Formula 4, wherein R is n-hexyl

EXAMPLE 13

Effect of the Catalysts on the Reaction of Metallic Silicon with a Mixture of 1-chlorohexane and Hydrogen Chloride The reaction was conducted using contact mixtures of Table 1 under the same condition as described in experiment No. 51 of Example 12, and the results are shown in Table 12.

TABLE 12

Effect of catalyst and co-catalysts on product distributions

| Exp. No. | Kind of contact mixture | Total amount of product (g) | Product Yield (%) | | | |
|---|---|---|---|---|---|---|
| | | | 1-chlorohexane | $III_c$ | $IV_c$ | hexene |
| 53 | I-1 | 12.3 | — | — | — | 46.0 |
| 54 | I-2 | 23.4 | 18.5 | 5.6 | 1.5 | 68.4 |
| 55 | I-3 | 32.0 | — | — | — | 98.2 |
| 56 | I-4 | 18.5 | 10.4 | 41.2 | 6.0 | 30.2 |
| 57 | I-5 | 31.2 | — | 10.2 | 7.2 | 80.6 |
| 58 | I-6 | 3.73 | 12.1 | 2.4 | 5.6 | 11.2 |
| 59 | I-7 | 7.37 | 15.3 | 28.2 | 1.9 | 11.1 |
| 60 | I-8 | 5.3 | 12.4 | 0.5 | — | 24.6 |

Amount of 1-chlorohexane in use: 10 ml, reaction time: 40 minutes
$III_c$: Compound of Formula 3, wherein R is n-hexyl
$IV_c$: Compound of Formula 4, wherein R is n-hexyl

EXAMPLE 14

The Product Compostion According to the Mixing Ratios of 1-chlorohexane and t-butyl Chloride The present experiement was described as shown in the following typical experimental No. 63 in Table 13. The reaction was carried out under the same condition as in Example 3, except that the same amount of t-butyl chloride was, used as the hydrogen chloride source. A mixture of 2-chloropropane and t-butyl chloride having the mixing ratio of 1:6 was reacted with metallic silicon at 280° C. to give 16.1 g of reaction products. The reaction products contained 5.9 g (45.2%) of 1,1-dichloro-1-silaheptane and 1.4 g (9.0%) of 1,1,1-trichloro-1-silaheptane. As other by-products, 31.1 g (13.2%) of 1-chlorohexane which is remained unreacted, 1.1 g (17.9%) of hexene, 2.5 g of trichlorosilane, and unconfirmed materials were obtained.

Table 13 shows the product compositions obtained by reacting a mixture of 1-chlorohexane and t-butyl chloride with metallic silicon, only with changing the mixing ratio of 1-chloropropane and t-butyl chloride.

TABLE 13

Mixing ratios of 1-chlorohexane and t-butyl chloride and product distributions

| Exp. No. | 1-chloro-hexane-t-butyl-chloride | Total amount of Product (g) | Product Yield (%) | | | |
|---|---|---|---|---|---|---|
| | | | 1-chlorohexane | $III_c$ | $IV_c$ | hexene |
| 61 | 1:2 | 9.5 | 6.5 | 36.3 | 7.1 | 12.8 |
| 62 | 1:4 | 13.2 | 7.5 | 43.7 | 8.9 | 15.3 |
| 63 | 1:6 | 16.1 | 13.2 | 45.2 | 9.0 | 17.9 |
| 64 | 1:8 | 12.3 | 13.1 | 29.9 | 5.8 | 8.2 |

Amount of 1-chlorohexane in use: 10 ml, reaction time: 40 minutes, reaction temperature: 280° C.
$III_c$: Compound of Formula 3, wherein R is n-hexyl
$IV_c$: Compound of Formula 4, wherein R is n-hexyl Since alkyldichlorosilanes prepared in accordance with the present invention can addtionally react with an organic compound having an unsaturated bond, they may be an important starting materials in preparing an organosilicon compound having various organic functional groups, and will be useful for the manufacture of silicones.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

What is claimed is:

1. A method for preparing alkyldichlorosilanes of Formula 3 by directly reacting metallic silicon with a mixture of alkyl chloride of Formula 1 and hydrogen chloride or alkyl chloride (Formula 2) which can generate hydrogen chloride at a reaction temperature in the presence of copper catalyst:

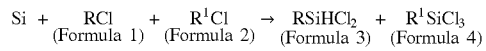

$$Si + \underset{\text{(Formula 1)}}{RCl} + \underset{\text{(Formula 2)}}{R^1Cl} \rightarrow \underset{\text{(Formula 3)}}{RSiHCl_2} + \underset{\text{(Formula 4)}}{R^1SiCl_3}$$

wherein, R is a linear, branched or cyclic $C_{3-10}$ alkyl group, $R^1$ is hydrogen or a primary secondary or tertiary $C_{4-6}$ alkyl group.

2. The method of claim 1, wherein 1 to 6 times of the compound in Formula 2 is added to each mole of alkyl chloride in Formula 1.

3. The method of claim 1, wherein said reactor is a fluidized bed reactor or a stirred reactor equipped with a spiral band agitator.

4. The method of claim 1, wherein said method further comprises adding 1 to 50% by weight of micro-spherical acid clay based on the amount of metallic silicon.

5. The method of any of the claims 1 to 4, wherein said method comprises using metal copper or copper compound which generates copper under the reaction condition in amount of 1 to 20% by weight for the amount of metallic silicon as a catalyst, and conducting the reaction at a temperature of 200–350° C. using metallic silicon having a size from 50 to 240 mesh.

6. The method of claim 5, wherein one or more co-catalysts which are selected from the group consisting of $NiCl_{12}$(dppm), $NiCl_2$(dppe), $NiCl_2$(dppb), $NiCl_2$(dppp), $NiCl_2$(dppd), Ni, Sn, Zn, Cd, Ca, Ti, Ag, Mg, Mn and the mixtures thereof are used in amount of 0.01 to 5% by weight for the amount of metallic silicon.

\* \* \* \* \*